United States Patent
Hayashi

(10) Patent No.: US 11,868,048 B2
(45) Date of Patent: Jan. 9, 2024

(54) NEGATIVE TYPE PHOTOSENSITIVE SILOXANE COMPOSITION AND METHODS FOR PRODUCING CURED FILM AND ELECTRONIC DEVICE USING THE SAME

(71) Applicant: Merck Patent GmbH, Darmstadt (DE)

(72) Inventor: Masanobu Hayashi, Kakegawa (JP)

(73) Assignee: Merck Patent GmbH, Darmstadt (DE)

( * ) Notice: Subject to any disclaimer, the term of this patent is extended or adjusted under 35 U.S.C. 154(b) by 359 days.

(21) Appl. No.: 16/767,250

(22) PCT Filed: Nov. 26, 2018

(86) PCT No.: PCT/EP2018/082475
§ 371 (c)(1),
(2) Date: May 27, 2020

(87) PCT Pub. No.: WO2019/101978
PCT Pub. Date: May 31, 2019

(65) Prior Publication Data
US 2020/0333708 A1  Oct. 22, 2020

(30) Foreign Application Priority Data

Nov. 27, 2017 (JP) .................................. 2017-226891

(51) Int. Cl.
| | | |
|---|---|---|
| *G03F 7/075* | (2006.01) | |
| *G03F 7/38* | (2006.01) | |
| *G03F 7/40* | (2006.01) | |
| *C07C 235/34* | (2006.01) | |
| *C07D 211/22* | (2006.01) | |
| *C08G 77/04* | (2006.01) | |
| *C09D 183/04* | (2006.01) | |
| *G03F 7/004* | (2006.01) | |
| *G03F 7/16* | (2006.01) | |
| *G03F 7/20* | (2006.01) | |
| *G03F 7/32* | (2006.01) | |

(52) U.S. Cl.
CPC .......... *G03F 7/0757* (2013.01); *C07C 235/34* (2013.01); *C07D 211/22* (2013.01); *C08G 77/04* (2013.01); *C09D 183/04* (2013.01); *G03F 7/0045* (2013.01); *G03F 7/162* (2013.01); *G03F 7/168* (2013.01); *G03F 7/2004* (2013.01); *G03F 7/322* (2013.01); *G03F 7/38* (2013.01); *G03F 7/40* (2013.01)

(58) Field of Classification Search
CPC . G03F 7/0757; G03F 7/30; G03F 7/38; G03F 7/40
See application file for complete search history.

(56) References Cited

U.S. PATENT DOCUMENTS

| | | | |
|---|---|---|---|
| 10,774,062 B2 * | 9/2020 | Sakai | ......................... C08F 2/50 |
| 2012/0183751 A1 * | 7/2012 | Katayama | ............. G03F 7/0387 |
| | | | 526/263 |
| 2017/0285477 A1 * | 10/2017 | Tanigaki | ............. H01L 21/3065 |

FOREIGN PATENT DOCUMENTS

| | | | | |
|---|---|---|---|---|
| EP | 2799928 A1 | 11/2014 | | |
| JP | 2006091815 A | 4/2006 | | |
| JP | 2012118523 A | 6/2012 | | |
| WO | WO-2017131047 A1 * | 8/2017 | ........... | C07C 279/26 |
| WO | WO-2017144148 A1 | 8/2017 | | |
| WO | WO-2017167690 A1 | 10/2017 | | |

OTHER PUBLICATIONS

International Preliminary Report on Patentability for PCT/EP2018/082475 date Feb. 14, 2019.

* cited by examiner

*Primary Examiner* — John S Chu
(74) *Attorney, Agent, or Firm* — Faegre Drinker Biddle & Reath LLP

(57) ABSTRACT

[Object] To provide a negative type photosensitive siloxane composition capable of forming a cured film excellent in heat resistance and critical thickness for cracking [Means] The present invention provides a negative type photosensitive siloxane composition comprising: a polysiloxane containing silanol in a specific content, a particular photo base generator, and a solvent. The content of silanol is measured by FT-IR.

17 Claims, 1 Drawing Sheet

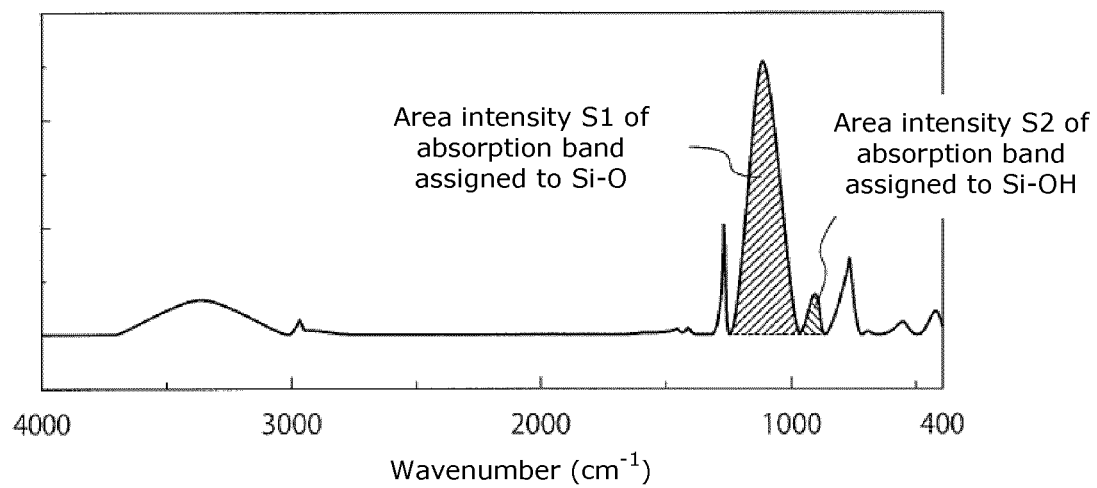

NEGATIVE TYPE PHOTOSENSITIVE SILOXANE COMPOSITION AND METHODS FOR PRODUCING CURED FILM AND ELECTRONIC DEVICE USING THE SAME

CROSS-REFERENCE TO RELATED APPLICATIONS

This application is a national stage application (under 35 U.S.C. § 371) of PCT/EP2018/082475, filed Nov. 26, 2018, which claims benefit of Japanese Application No. 2017-226891, filed Nov. 27, 2017, both of which are incorporated herein by reference in their entirety.

BACKGROUND OF THE INVENTION

Technical Field

The present invention relates to a negative type photosensitive siloxane composition. Further, this invention also relates to methods for producing a cured film and an electronic device using the same.

Background Art

In semiconductor devices and displays, various insulating films are provided. Those insulating films are required to have insulating and heat-resistant properties so that the devices and displays may have excellent characteristics. To meet the requirement, SOG films and silicon dioxide films formed by chemical vapor deposition have been conventionally adopted.

However, those films are not photosensitive. Accordingly, in order to form a pattern on the insulating film, it is necessary to form a resist pattern on the film surface by lithography and then to perform an etching process in which the resist pattern serves as a mask.

As a means for forming a favorable insulating film without the above complicated procedures, a method is proposed in which a photosensitive siloxane composition is employed. If the insulating film is formed from the photosensitive siloxane composition, the above procedures such as etching are unnecessary and consequently the production cost can be reduced.

However, insulating films obtained from conventionally proposed photosensitive siloxane compositions are liable to suffer from cracking when they are thickly formed. In addition, they have room for improvement in view of heat resistance.

PRIOR ART DOCUMENTS

Patent Documents

[Patent document 1] Japanese Patent Laid-Open No. 2006-091815

SUMMARY OF THE INVENTION

Problem to be Solved by the Invention

The present invention aims to solve the above problem remaining to be improved in the prior art, and specifically aims to provide a photosensitive composition capable of easily forming a thick and highly heat-resistant cured film.

Means for Solving Problem

The negative type photosensitive siloxane composition according to the present invention comprises:

(I) a polysiloxane which contains a repeating unit represented by the following formula (Ia):

$$\begin{array}{c} R^1 \\ | \\ \text{---}(O_{0.5}\text{---}Si\text{---}O_{0.5})\text{---} \\ | \\ O_{0.5} \\ | \end{array} \quad \text{(Ia)}$$

wherein $R^1$ is hydrogen, a monovalent to trivalent, linear, branched or cyclic, saturated or unsaturated $C_{1\text{-}30}$ aliphatic hydrocarbon group, or a monovalent to trivalent $C_{6\text{-}30}$ aromatic hydrocarbon group, in said aliphatic hydrocarbon group and said aromatic hydrocarbon group, one or more methylene are unsubstituted or substituted with oxy, imide or carbonyl, one or more hydrogens are unsubstituted or substituted with fluorine, hydroxy or alkoxy, or one or more carbons are unsubstituted or substituted with silicon, when $R^1$ is divalent or trivalent, $R^1$ connects S1 atoms contained in a plurality of repeating units; and a repeating unit represented by the following formula (Ib):

$$\begin{array}{c} | \\ O_{0.5} \\ | \\ \text{---}(O_{0.5}\text{---}Si\text{---}O_{0.5})\text{---} \\ | \\ O_{0.5} \\ | \end{array} \quad \text{(Ib)}$$

and further which shows a spectrum in which the area intensities S1 and S2 of the peaks in the ranges of $1100\pm100\ \text{cm}^{-1}$ and $900\pm100\ \text{cm}^{-1}$ assigned to Si—O and SiOH, respectively, are in a S2/S1 ratio of 0.05 to 0.15 when measured and analyzed by FT-IR, (II) a photo base generator represented by the following formula (PBG-A) or (PBG-B):

(PBG-A)

[Chemical structure showing a benzene ring with substituents $R^{41}$, $R^{42}$, $R^{43}$, $R^{44}$, HO, connected via $R^{45}$=$R^{46}$ to a carbonyl group C(=O)—N($R^{47}$)($R^{48}$)]

-continued

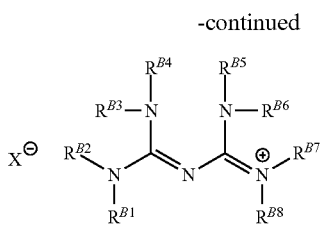
(PBG-B)

wherein
each of $R^{A1}$ to $R^{A6}$ is independently hydrogen, halogen, hydroxy, mercapto, sulfide, silyl, silanol, nitro, nitroso, sulfino, sulfo, sulfonate, phosphino, phosphinyl, phosphono, phosphonato, amino, ammonium, an unsubstituted or substituted $C_{1-20}$ aliphatic hydrocarbon group, an unsubstituted or substituted $C_{6-22}$ aromatic hydrocarbon group, unsubstituted or substituted $C_{1-20}$ alkoxy, or unsubstituted or substituted $C_{6-20}$ aryloxy;
each of $R^{A7}$ and $R^{A8}$ is independently $C_{1-6}$ hydroxyalkyl, or otherwise $R^{A7}$ and $R^{A8}$ are connected to each other via a $C_{2-9}$ alkylene to form a cyclic structure to which a $C_{1-6}$ hydroxyalkyl is connected;
each of $R^{B1}$ to $R^{B8}$ is independently hydrogen, an unsubstituted or substituted $C_{1-20}$ aliphatic hydrocarbon group, an unsubstituted or substituted $C_{6-22}$ aromatic hydrocarbon group, unsubstituted or substituted $C_{1-20}$ alkoxy, or unsubstituted or substituted $C_{6-20}$ aryloxy; and
$X^-$ is a borate or carboxylate ion having an unsubstituted or substituted $C_{1-20}$ aliphatic hydrocarbon group or an unsubstituted or substituted $C_{6-22}$ aromatic hydrocarbon group; and
(III) a solvent.

Further, the method for producing a cured film according to the present invention comprises: coating a substrate with the above negative type photosensitive composition, exposing the substrate to light, then developing and heating the substrate.

Furthermore, the method for producing an electronic device according to the present invention includes the above method for producing a cured film.

Effect of the Invention

The photosensitive siloxane composition of the present invention makes it possible to easily form a cured film that is thick and highly heat resistant enough to be suitable as an insulating film or the like in displays or electronic devices.

BRIEF DESCRIPTION OF THE DRAWINGS

FIG. 1 is an example of IR absorption spectrum shown by the polysiloxane usable in the present invention.

DETAILED DESCRIPTION OF THE INVENTION

Mode for Carrying Out the Invention

Embodiments of the present invention are described in detail below.

Unless otherwise stated in the present specification, when numerical ranges are indicated using "to", they include both endpoints, and units thereof are common. For example, 5 to 25 mol % means 5 mol % or more and 25 mol % or less.

In the present specification, the descriptions such as "$C_{x-y}$", "$C_x$-$C_y$" and "$C_x$" mean the number of carbons in the molecule or substituent. For example, $C_{1-6}$ alkyl means alkyl having 1 or more and 6 or less carbons (methyl, ethyl, propyl, butyl, pentyl, hexyl etc.). In the present specification, the fluoroalkyl refers to one in which one or more hydrogens in alkyl are replaced with fluorine, and the fluoroaryl refers to one in which one or more hydrogens in aryl are replaced with fluorine.

Also, unless otherwise stated in the present specification, alkyl means linear or branched alkyl and cycloalkyl means alkyl having a cyclic structure. Cycloalkyl includes alkyl having a cyclic structure which contains a linear or branched alkyl substituent. Hydrocarbon means a monovalent or divalent or more valent group which includes carbon and hydrogen, and optionally oxygen or nitrogen. Aliphatic hydrocarbon means a linear, branched or cyclic aliphatic hydrocarbon group. Aromatic hydrocarbon contains an aromatic ring and may have, if necessary, an aliphatic hydrocarbon group as a substituent. These aliphatic and aromatic hydrocarbon groups optionally contain fluorine, oxy, hydroxy, amino, carbonyl or silyl and the like.

In the present specification, when polymer has plural types of repeating units, these repeating units copolymerize. These copolymerizations are any of alternating copolymerization, random copolymerization, block copolymerization, graft copolymerization, or a mixture thereof.

Also, unless otherwise stated in the present specification, Celsius is used as the temperature unit. For example, 20 degrees means 20 degrees Celsius.

<Photosensitive Siloxane Composition>

The photosensitive siloxane composition according to the present invention comprises:
(I) a polysiloxane,
(II) a photo base generator, and
(III) a solvent.

These components are respectively described below.

[(I) Polysiloxane]

The polysiloxane refers to a polymer having a main chain of Si—O—Si bond (siloxane bond). In the present specification, the polysiloxane shall also include a silsesquioxane polymer represented by the general formula $(RSiO_{1.5})_n$.

The polysiloxane according to the present invention comprises two types of repeating units represented by specific formulas. The first repeating unit is represented by the following formula (Ia):

(Ia)

In the above formula, $R^1$ is hydrogen, a monovalent to trivalent, linear, branched or cyclic, saturated or unsaturated $C_{1-30}$ aliphatic hydrocarbon group, or a monovalent to trivalent $C_{6-30}$ aromatic hydrocarbon group. In the aliphatic hydrocarbon group and the aromatic hydrocarbon group, one or more methylene are unsubstituted or substituted with oxy, imide or carbonyl, one or more hydrogens are unsubstituted or substituted with fluorine, hydroxy or alkoxy, or one or more carbons are unsubstituted or substituted with silicon. When $R^1$ is divalent or trivalent, $R^1$ connects Si atoms contained in a plurality of repeating units.

When $R^1$ is a monovalent group, $R^1$ is preferably hydrogen, linear, branched or cyclic $C_{1-6}$ alkyl or $C_{6-10}$ aryl. Examples thereof include: (i) hydrogen; (ii) alkyl, such as, methyl, ethyl, propyl, butyl, pentyl, hexyl, heptyl, octyl, or decyl; (iii) cycloalkyl, such as, cyclohexyl; (iv) aryl, such as, phenyl, tolyl, or benzyl; (v) fluoroalkyl, such as, trifluoromethyl, 2,2,2-trifluoroethyl, or 3,3,3-trifluoropropyl; (vi) fluoroaryl; and (vii) nitrogen-containing group having an amino or imido structure, such as, glycidyl, isocyanate or amino. Preferred are (ii) alkyl and (iv) aryl, and particularly preferred are methyl and phenyl.

When $R^1$ is a divalent or trivalent group, $R^1$ preferably contains alkylene, arylene, cycloalkylene ring, piperidine ring, pyrrolidine ring, isocyanurate ring and the like.

The second repeating unit is represented by the following formula (Ib):

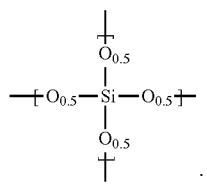
(Ib)

Specifically, the polysiloxane preferably comprises repeating units selected from the group consisting of (i-1), (i-2) and (i-3) in combination:

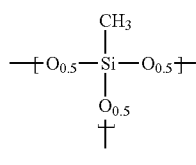
(i-1)

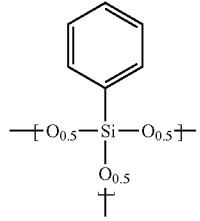
(i-2)

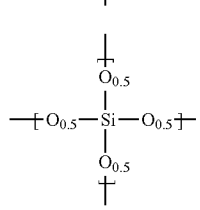
(i-3)

provided that the mixing molar ratios p1, p2 and p3 of (i-1), (i-2) and (i-3), respectively, satisfy the conditions of:

$0.4 \leq p1 \leq 0.8$, $0 \leq p2 \leq 0.4$, and $0.2 \leq p3 \leq 0.6$.

If this polysiloxane is employed, it is possible to obtain a thick cured film remarkably improved in heat resistance and in critical thickness for cracking. The smaller the molar ratio P2 is, the more the heat resistance tends to be improved. Accordingly, in view of heat resistance, the molar ratio P2 is preferably equal to 0 (i.e., p2=0).

The polysiloxane adopted in the present invention is characterized not only by the types of repeating units constituting the molecule thereof but also by the amount of silanol groups contained therein. A polysiloxane molecule has a silanol structure (SiOH) at the terminal or in the side chain. The amount of silanol groups depends on synthesis conditions of polysiloxane, such as, mixing ratios of monomers and kinds of reaction catalysts. The silanol content can be quantitively determined by IR absorption spectroscopy. In the IR absorption spectrum, the absorption band assigned to silanol (SiOH) has a peak in the range of $900 \pm 100$ cm$^{-1}$. Accordingly, if a large amount of silanol groups are contained, that absorption band has high intensity.

In the present invention, the intensity of the absorption band assigned to Si—O is used as a reference for quantitively evaluating the silanol content. Specifically, the absorption band having a peak in the range of $1100 \pm 100$ cm$^{-1}$ is adopted as the peak assigned to Si—O. The area intensities S1 and S2 of the absorption bands assigned to Si—O and SiOH, respectively, are measured to calculate the S2/S1 ratio, and thereby the silanol content is relatively evaluated. In consideration of realizing pattern formation, the S2/S1 ratio is preferably a large value. On the other hand, however, in consideration of forming a pattern stably, the S2/S1 ratio is preferably a small value. In view of those considerations, the S2/S1 ratio is 0.05 to 0.15, preferably 0.06 to 0.13 in the present invention.

In determining the area intensities of the absorption bands, noises and the like in the IR absorption spectrum are taken into account. FIG. 1 shows a typical IR absorption spectrum of the polysiloxane usable in the present invention. In the spectrum, an absorption band assigned to SiOH has a peak in the range of $900 \pm 100$ cm$^{-1}$ and one assigned to Si—O has a peak in the range of $1100 \pm 100$ cm$^{-1}$. As shown in the figure, the area intensities of those absorption bands are measured as areas based on the baseline that is determined in consideration of noises and the like. The absorption bands assigned to SiOH and Si—O may be overlapped in their tail regions. In that case, the wavenumber at the local minimum point between the peaks is regarded as the boundary. If the band assigned to SiOH or Si—O is overlapped with other band tails, the boundary is determined in the same manner.

Such a polysiloxane can be obtained through hydrolysis and condensation, optionally in the presence of an acidic catalyst or a basic catalyst, of silane compounds represented by the following formulas (ia) and (ib):

$$R^{1'}[Si(OR^2)_3]_p \quad \text{(ia)}$$

$$Si(OR^2)_4 \quad \text{(ib)}$$

wherein p is an integer of 1 to 3, $R^{1'}$ is hydrogen, a monovalent to trivalent, linear, branched or cyclic, saturated or unsaturated $C_{1-30}$ aliphatic hydrocarbon group, or a monovalent to trivalent, $C_{6-30}$ aromatic hydrocarbon group, in said aliphatic hydrocarbon group and said aromatic hydrocarbon group, one or more methylene are unsubstituted or substituted with oxy, imide or carbonyl, one or more hydrogens are unsubstituted or substituted with fluorine, hydroxy or alkoxy, or one or more carbons are unsubstituted or substituted with silicon, and $R^2$ represents $C_{1-10}$ alkyl.

Each of the silane compounds (ia) and (ib) can be used in combination of two or more kinds.

In the process for producing the polysiloxane, the blending ratio of the silane compound (ib) to the total molar amount of the silane compounds can be changed to control the mixing ratio of the repeating units in the polysiloxane and to control the above S2/S1 ratio. In view of heat resistance, the polysiloxane in the present invention contains the repeating unit (Ib) in a mixing ratio of preferably 20 mol % or more, further preferably 30 mol % or more based on the total amount of the repeating units. However, in order to avoid precipitation of the silane compounds and to prevent sensitivity deterioration of the formed cured film, the mixing ratio of the repeating unit (Ib) is preferably 70 mol % or less, more preferably 60 mol % or less.

The mass average molecular weight of the polysiloxane is usually 1,000 to 12,000, and preferably 1,000 to 10,000 from the viewpoint of solubility in an organic solvent and solubility in an alkali developing solution. The mass average molecular weight in terms of polystyrene can be measured by gel permeation chromatography based on polystyrene.

[(II) Photo Base Generator]

The composition according to the present invention is a negative type photosensitive composition, in which the exposed portion becomes insoluble in an alkali developing solution by action of a photosensitive component.

The negative type photosensitive composition according to the present invention contains a photo base generator as the photosensitive component. The photo base generator is represented by the following formula (PBG-A) or (PBG-B):

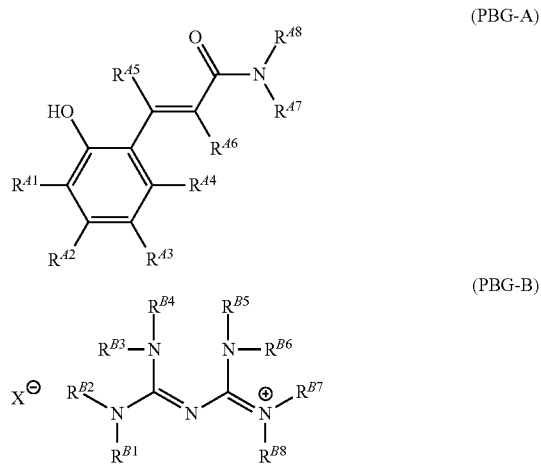

In the formulas, each of $R^{A1}$ to $R^{A6}$ is independently hydrogen, halogen, hydroxy, mercapto, sulfide, silyl, silanol, nitro, nitroso, sulfino, sulfo, sulfonate, phosphino, phosphinyl, phosphono, phosphonato, amino, ammonium, an unsubstituted or substituted $C_{1-20}$ aliphatic hydrocarbon group, an unsubstituted or substituted $C_{6-22}$ aromatic hydrocarbon group, unsubstituted or substituted $C_{1-20}$ alkoxy, or unsubstituted or substituted $C_{6-20}$ aryloxy;

each of $R^{A7}$ and $R^{A8}$ is independently $C_{1-6}$ hydroxyalkyl, or otherwise $R^{A7}$ and $R^{A8}$ are connected to each other via a $C_{2-9}$ alkylene to form a cyclic structure to which a $C_{1-6}$ hydroxyalkyl is connected;

each of $R^{B1}$ to $R^{B8}$ is independently hydrogen, an unsubstituted or substituted $C_{1-20}$ aliphatic hydrocarbon group, an unsubstituted or substituted $C_{6-22}$ aromatic hydrocarbon group, unsubstituted or substituted $C_{1-20}$ alkoxy, or unsubstituted or substituted $C_{6-20}$ aryloxy; and $X^-$ is a borate or carboxylate ion having an unsubstituted or substituted $C_{1-20}$ aliphatic hydrocarbon group or an unsubstituted or substituted $C_{6-22}$ aromatic hydrocarbon group.

Among the above, each of $R^{A1}$ to $R^{A4}$ is preferably hydrogen, hydroxy, a $C_{1-6}$ aliphatic hydrocarbon group, $C_{1-6}$ alkoxy, $C_{1-6}$ alkylamino or di($C_{1-6}$ alkyl)amino. Each of $R^{A5}$ and $R^{A6}$ is preferably hydrogen.

Two or more of $R^{A1}$ to $R^{A4}$ are or are not connected to form a cyclic structure, which can contain a hetero atom.

Hydroxy is included in or connected to $R^{A7}$ and $R^{A8}$. In some cases, each of $R^{A7}$ and $R^{A8}$ individually contains hydroxy. In other cases, $R^{A7}$ and $R^{A8}$ are connected to each other via an alkylene to form a cyclic structure to which hydroxy is linked via an alkylene. Hydroxy or hydroxyalkyl is connected. The alkylene is $C_{1-20}$ which can have a substituent and further can have $C_{1-6}$ aliphatic hydrocarbon group.

It is preferred to select $R^{A1}$ to $R^{A4}$ properly according to the employed exposure wavelength. For use in displays, preferred are alkoxy, nitro, alkylamino, dialkylamino and unsaturated hydrocarbon-linking functional groups, such as vinyl and alkynyl. Those groups have a function of shifting the absorption wavelength to the g-, h- or i-line region. Among them, methoxy and ethoxy are particularly preferred.

Each of $R^{B1}$ to $R^{B8}$ is independently hydrogen, an unsubstituted or substituted $C_{1-20}$ aliphatic hydrocarbon group, an unsubstituted or substituted $C_{6-22}$ aromatic hydrocarbon group, unsubstituted or substituted $C_{1-20}$ alkoxy, or unsubstituted or substituted $C_{6-20}$ aryloxy. Adjacent two of $R^{B1}$ to $R^{B8}$ can be connected to each other via an alkylene to form a cyclic structure.

In the formula, $X^-$ is a borate or carboxylate ion having an unsubstituted or substituted $C_{1-20}$ aliphatic hydrocarbon group or an unsubstituted or substituted $C_{6-22}$ aromatic hydrocarbon group. Examples thereof include: butyl-triphenylborate ion, tetraphenylborate ion, butyl-tri(p-tolyl)phenyl borate, tetrakis(4-fluorophenyl) borate ion, 2-(3-benzoylphenyl) and propionate ion.

The photo base generator is a compound generating base under light exposure and is presumed to contribute toward polymerization of the polysiloxane. Consequently, the photo base generator makes it possible to form a patterned cured film by exposure and development. There is an advantage of reducing damages to circuits and elements on device production by eliminating dry etching at the pattern processing. There are no restrictions on the mechanism of how the photo base generator generates base. Accordingly, the base is generated simply by a photochemical reaction, or otherwise a chemical reaction is induced by energy, such as heat, to generate the base after the generator molecule changes the structure thereof under light exposure. The compound represented by the formula (PBG-A) is presumed to go through the latter process.

Examples of the photo base generator are as follows.

(PBG-A1)
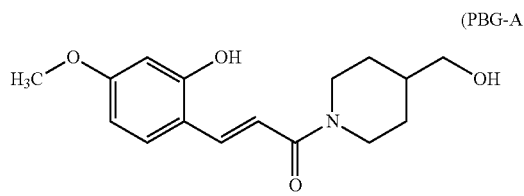

(PBG-A2)
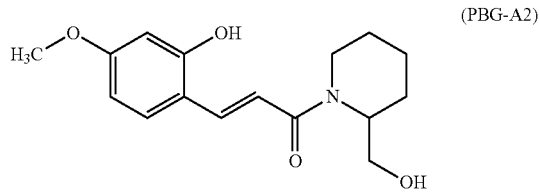

(PBG-A3)
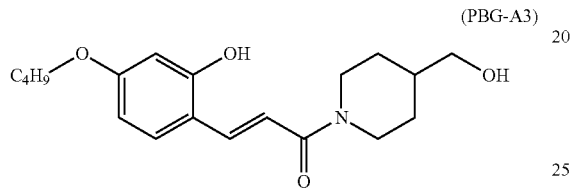

(PBG-A4)
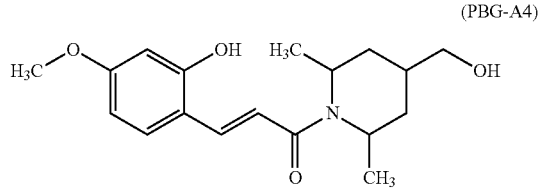

(PBG-A5)
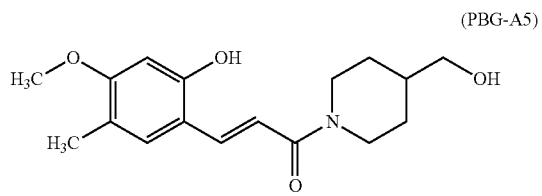

(PBG-A6)
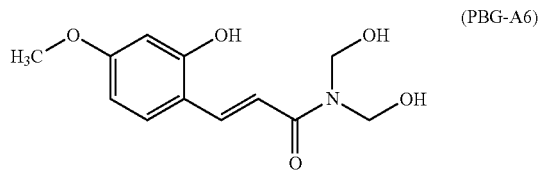

(PBG-A7)
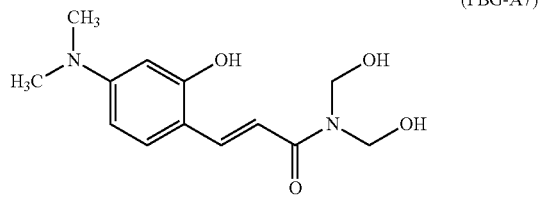

(PBG-A8)
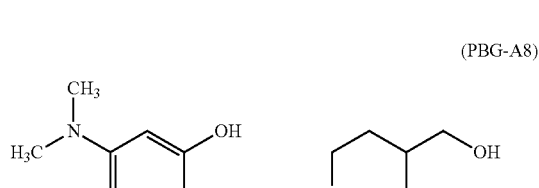

(PBG-B1)
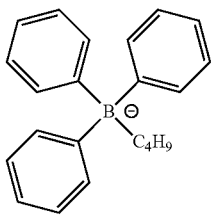

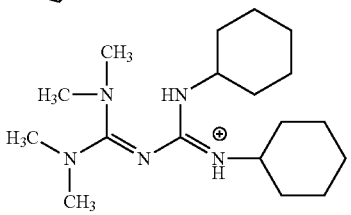

(PBG-B2)
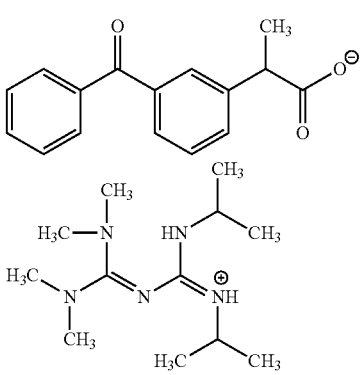

The photo base generator represented by the formula (PBG-A) is preferably used in the form of a hydrate. If the photo base generator is used in the form of a hydrate, preferred effects tend to be obtained as compared with that in the form of an anhydrate. Here, the "anhydrate" means a compound that is not hydrated. There are no particular restrictions on how to hydrate an anhydrate of the photo base generator, and known methods can be adopted. For example, the photo base generator anhydrate is added to water under the condition where the amount of water is 10 times or more the mole of the anhydrate, and then the solution is stirred for about 1 hour at room temperature or above. Subsequently, excess of the solvent is distilled off from the obtained mixture with an evaporator, to obtain the hydrate. It can be verified by infrared (IR) absorption spectroscopy, by $^1$H-NMR or by thermogravimetry differential thermal analysis (TG-DTA) whether the resultant product is hydrated or not.

In another way, the photo base generator of the formula (PBG-A) in the form of an anhydrate can be mixed with water, stirred and then directly used without isolating the hydrate.

The amount of water for hydration is 0.1 mol or more, preferably 1 mol or more based on 1 mol of the photo base generator represented by the formula (PBG-A).

The amount of the photo base generator depends on the kind of the active substance released by decomposition thereof, on the amount of the released substance, on the required sensitivity and on the required dissolution contrast between the exposed and unexposed portions. However, the amount is preferably 0.1 to 5.0 mass %, more preferably 0.5 to 2.0 mass %, based on the mass of the polysiloxane. Here, if the photo base generator is used in the form of a hydrate, the mass of the photo base generator does not include that of the hydrated water. From the viewpoint of promoting polymerization of the polysiloxane, the photo base generator is preferably incorporated in a large amount. On the other hand, from the viewpoint of avoiding cracks and coloring of the coating film, the amount thereof is preferably small.

[(III) solvent]

The composition according to the invention comprises a solvent. This solvent is selected from those which uniformly dissolve or disperse each component contained in the composition, and is generally an organic solvent. Specific examples of the solvent include ethylene glycol monoalkyl ethers such as ethylene glycol monomethyl ether, ethylene glycol monoethyl ether, ethylene glycol monopropyl ether and ethylene glycol monobutyl ether; diethylene glycol dialkyl ethers such as diethylene glycol dimethyl ether, diethylene glycol diethyl ether, diethylene glycol dipropyl ether and diethylene glycol dibutyl ether; ethylene glycol alkyl ether acetates such as methyl cellosolve acetate and ethyl cellosolve acetate; propylene glycol monoalkyl ethers such as propylene glycol monomethyl ether (PGME) and propylene glycol monoethyl ether; propylene glycol alkyl ether acetates such as propylene glycol monoethyl ether acetate (PGMEA), propylene glycol monoethyl ether acetate and propylene glycol monopropyl ether acetate; aromatic hydrocarbons such as benzene, toluene and xylene; ketones such as methyl ethyl ketone, acetone, methyl amyl ketone, methyl isobutyl ketone and cyclohexanone; and alcohols such as isopropanol and propane diol. These solvents are used alone or in combination of two or more kinds.

The mixing ratio of the solvent varies depending on the application method and the demand for the film thickness after coating. For example, in the case of spray coating, the concentration is relatively high, but in the case of slit coating for manufacturing displays, the concentration is lower. The total ratio of the above polysiloxane, photo base generator, and other optional components described below based on the whole mass of the composition, namely, the solid content is generally 2.0 to 50 mass %, preferably 10 to 40 mass %.

[(IV) optional component]

In addition, the composition according to the present invention can contain optional components as needed. Examples of such optional components include curing aids. As the curing aids, photo acid generators and photo base generators different from those described above can be employed. They are selected according to polymerization reactions or crosslinking reactions conducted in the process for producing the cured film.

Examples of the photo acid generators, which can be arbitrarily selected from commonly used ones, include diazomethane compounds, triazine compounds, sulfonic acid esters, diphenyliodonium salts, triphenylsulfonium salts, sulfonium salts, ammonium salts, phosphonium salts, sulfonimide compounds, and the like.

Examples of the above photo base generator include mufti-substituted amide compounds having an amide group, lactams, imide compounds or ones containing its structure. In addition, an ionic photo base generator including, as anion, an amide anion, a methide anion, a borate anion, a phosphate anion, a sulfonate anion, a carboxylate anion, or the like can also be used.

Here, the "photo" means, for example, visible light, UV rays or IR rays. The curing aid is preferably a compound generating acid or base under exposure of UV rays employed for manufacturing thin film transistors.

The amount of the curing aid depends on the kind of the active substance released by decomposition of the curing aid, on the amount of the released substance, on the required sensitivity and on the required dissolution contrast between the exposed and unexposed portions. However, the amount is preferably 0.001 to 10 mass parts, more preferably 0.01 to 5 mass parts, based on 100 mass parts of the polysiloxane. If the amount is 0.001 mass part or more, the dissolution contrast between the exposed and unexposed portions is high enough to obtain a favorable effect of the curing aid. On the other hand, if it is 10 mass parts or less, the formed film hardly suffers from cracks and is not colored by decomposition of the curing aid, so that the coating film is improved in colorless transparency.

The curing aid can be a thermal acid generator or a thermal base generator. Examples of the thermal acid generators include salts and esters that generate organic acids, such as various aliphatic sulfonic acids and salts thereof, various aliphatic carboxylic acids such as citric acid, acetic acid and maleic acid and salts thereof, various aromatic carboxylic acids such as benzoic acid and phthalic acid and salts thereof, aromatic sulfonic acids and ammonium salts thereof, various amine salts, aromatic diazonium salts, and phosphonic acids and salts thereof. Among the thermal acid generators, in particular, it is preferably a salt composed of an organic acid and an organic base, further preferably a salt composed of sulfonic acid and an organic base.

Preferred sulfonic acids include p-toluenesulfonic acid, benzenesulfonic acid, p-dodecylbenzenesulfonic acid, 1,4-naphthalenedisulfonic acid, methanesulfonic acid, and the like. These acid generators can be used alone or in combination.

Examples of the thermal base generators include compounds that generate bases such as imidazole, tertiary amine and quaternary ammonium, and mixtures thereof. Examples of the bases to be released include imidazole derivatives such as N-(2-nitrobenzyloxycarbonyl) imidazole, N-(3-nitrobenzyloxycarbonyl) imidazole, N-(4-nitrobenzyloxycarbonyl) imidazole, N-(5-methyl-2-nitrobenzyloxycarbonyl) imidazole and N-(4-chloro-2-nitrobenzyloxycarbonyl) imidazole, and 1,8-diazabicyclo[5.4.0]undecene-7. Like the acid generators, these base generators can be used alone or in combination.

Other optional components are, for example, surfactants and the like.

Since the surfactant can improve coatability, it is preferable to be used. Examples of the surfactant that can be used in the siloxane composition of the present invention include nonionic surfactants, anionic surfactants, amphoteric surfactants, and the like.

Examples of the nonionic surfactant include, polyoxyethylene alkyl ethers, such as polyoxyethylene lauryl ether, polyoxyethylene oleyl ether and polyoxyethylene cetyl ether; polyoxyethylene fatty acid diester; polyoxy fatty acid monoester; polyoxyethylene polyoxypropylene block polymer; acetylene alcohol; acetylene glycol; acetylene alcohol derivatives, such as polyethoxylate of acetylene alcohol; acetylene glycol derivatives, such as polyethoxylate of acetylene glycol; fluorine-containing surfactants, such as Fluorad (trade name, manufactured by Sumitomo 3M Limited), Megafac (trade name, manufactured by DIC Corporation), Surufuron (trade name, Asahi Glass Co., Ltd.); or organosiloxane surfactants, such as KP341 (trade name, manufactured by Shin-Etsu Chemical Co., Ltd.). Examples of said acetylene glycol include 3-methyl-1-butyne-3-ol, 3-methyl-1-pentyn-3-ol, 3,6-dimethyl-4-octyne-3,6-diol, 2,4,7,9-tetramethyl-5-decyne-4,7-diol, 3,5-dimethyl-1-hexyne-3-ol, 2,5-dimethyl-3-hexyne-2,5-diol, 2,5-dimethyl-2,5-hexane-diol and the like.

Further, examples of the anionic surfactant include ammonium salt or organic amine salt of alkyl diphenyl ether disulfonic acid, ammonium salt or organic amine salt of alkyl diphenyl ether sulfonic acid, ammonium salt or organic amine salt of alkyl benzene sulfonic acid, ammonium salt or organic amine salt of polyoxyethylene alkyl ether sulfuric acid, ammonium salt or organic amine salt of alkyl sulfuric acid and the like.

Further, examples of the amphoteric surfactant include 2-alkyl-N-carboxymethyl-N-hydroxyethyl imidazolium betaine, lauric acid amide propyl hydroxysulfone betaine and the like.

These surfactants can be used alone or as a mixture of two or more kinds, and the mixing ratio thereof is usually 50 to 10,000 ppm, preferably 100 to 5,000 ppm, based on the total mass of the photosensitive siloxane composition.

<Methods for Producing a Cured Film and an Electronic Device Comprising the Same>

The cured film according to the present invention can be produced by the steps of coating a substrate with the above-described composition, exposing the substrate to light, then developing and heating the substrate.

Formation of the coating film of the composition in the present invention can be carried out by a generally known method, such as, dip coating, roll coating, bar coating, brush coating, spray coating, doctor coating, flow coating, spin coating, slit coating and the like. As the substrate, a suitable substrate such as a silicon substrate, a glass substrate, a resin film, or the like can be used. When the substrate is a film, gravure coating can also be used. If desired, a drying process can be additionally set after coating the film. The coating process can be repeated once or twice or more to make the film thickness of the formed coating film as desired.

The composition according to the present invention can form a thick cured film, and hence it is possible to obtain a relatively thick coating film.

After forming the coating film of the composition according to the present invention, it is preferable to carry out pre-baking (heat treatment) of the coating film in order to dry the coating film and reduce the residual amount of the solvent. The pre-baking process can be generally carried out at a temperature of 70 to 150° C., preferably 90 to 120° C., in the case of a hot plate, for 10 to 180 seconds, preferably 30 to 90 seconds and in the case of a clean oven, for 1 to 30 minutes.

Since the composition of the present invention has photosensitivity, it can form a patterned cured film. The process for forming the pattern is described below. The desired pattern is formed by the steps of: forming a coating film of the composition according to the present invention, pre-baking and then pattern-wise irradiating said film with light. As the light source, a high-pressure mercury lamp, a low-pressure mercury lamp, a lamp such as metal halide or xenon, a laser diode, an LED or an excimer laser equipment can be employed. Ultraviolet rays such as g-line, h-line, i-line and KrF excimer laser light are usually used as the irradiation light. It is general to use light of 248 nm (KrF excimer laser equipment) or 365 nm (high-pressure mercury lamp) for patterning. The energy of the irradiation light is generally 10 to 2,000 mJ/cm$^2$, preferably 20 to 1,000 mJ/cm$^2$, although it depends on the light source and the film thickness of the coating film. If the irradiation light energy is lower than 10 mJ/cm$^2$, the composition does not decompose sufficiently in some cases. On the other hand, when the irradiation light energy is higher than 2,000 mJ/cm$^2$, the exposure becomes excess and halation is generated.

In order to irradiate light in a pattern shape, a general photomask can be used. Such a photomask is well known to those skilled in the art. The environment at the time of irradiation is not particularly limited, and generally it can be set as an ambient atmosphere (in the air) or nitrogen atmosphere. In the case of forming a film on the entire surface of the substrate, light irradiation can be performed to the entire surface of the substrate. In the present invention, the pattern film also includes such a case where a film is formed on the entire surface of the substrate.

After the exposing step, post-exposure baking can be carried out according to necessity with the aim of promoting interpolymer reactions by the base generated in the exposed portion. This heating treatment differs from the below-described heating step in that it is not for the purpose of curing the coating film completely but for the purpose of making it possible to leave a desired pattern on the substrate after development and to remove the part other than the pattern by development.

When the post-exposure baking step is carried out, it is possible to use a hot-plate, an oven, a furnace or the like. The heating temperature should not be too high because it is unfavorable for the base generated by exposure in the exposed portion to diffuse into the unexposed portion. In view of that, the temperature of post-exposure baking is preferably 60 to 200° C., more preferably 80 to 180° C. If necessary, the temperature can be step-by-step increased so as to control the curing speed of the composition. There are no particular restrictions on the atmosphere of baking. In order to control the curing speed of the composition, the atmosphere can be selected from, for example, an atmosphere of inert gas such as nitrogen gas, a vacuum atmosphere, a reduced-pressure atmosphere, an oxygen gas atmosphere or the like. The baking time is preferably longer than a certain period so as to keep higher uniformity of thermal budget in the wafer surface, but also preferably not excessively long so as to prevent the diffusion of base. In consideration of those, the baking time is preferably 20 to 500 seconds, more preferably 30 to 300 seconds.

As the developing solution to be used at the time of development, any developing solution conventionally used for developing the photosensitive siloxane composition can be used. Preferable examples of the developing solution include an alkali developing solution which is an aqueous solution of an alkaline compound such as tetraalkylammonium hydroxide, choline, alkali metal hydroxide, alkali metal metasilicate (hydrate), alkali metal phosphate (hydrate), aqueous ammonia, alkylamine, alkanolamine and heterocyclic amine, and a particularly preferable alkali developing solution is a tetramethylammonium hydroxide aqueous solution. In the alkali developing solution, a water-soluble organic solvent such as methanol, ethanol, or a surfactant can be further contained, if necessary. After development with the alkali developing solution, washing with water is normally carried out.

Thereafter, an entire surface exposure (flood exposure) process is usually performed. In the entire surface exposure process, the photo acid or base generator receives radiated light and releases acid or base, respectively. As the method of entire surface exposure, there is a method for exposing light over the entire surface with about 100 to 2,000 mJ/cm$^2$ (in terms of exposure amount at wavelength of 365 nm) using an ultraviolet visible exposure machine such as an aligner (for example, PLA-501F manufactured by Canon Inc.).

After development, the obtained patterned film is cured by heating. The heating temperature is usually 500° C. or more, preferably 600° C. or more.

The cured film obtained according to the present invention is characterized by having high heat resistance. Further, the composition of the present invention can form a cured film having larger critical thickness for cracking, as compared with films formed from conventional compositions. Specifically, the cured film obtained from the composition of the present invention rarely suffers from cracks even if formed as thick as 1.0 µm or more.

The cured film thus formed can be suitably utilized in many fields, not only as a planarization film, an interlayer insulating film, a transparent protective film and the like for various devices such as a flat panel display (FPD) but also as an interlayer insulating film for low temperature polysilicon or a buffer coat film for IC chip and the like. Further, the cured film can be also used as an optical device material or the like.

EXAMPLES

The present invention will be further specifically explained by use of the following examples.

Synthesis Example 1 (Synthesis of Photo Base Generator PBG-A1)

In a 50 mL flask, 3.44 g (8 mmol) of ethoxycarbonylmethyl(triphenyl)phosphonium bromide and 1.22 g (8 mmol) of 2-hydroxy-4-methoxybenzaldehyde were mixed and dissolved in 10 mL of methanol to prepare a material mixture.

Independently, 4.00 g of potassium carbonate and 30 mL of methanol were placed in a 200 mL four-necked flask equipped with a stirrer and a dropping funnel. While they were kept stirred, the material mixture was slowly dropped therein.

After the dropping was completed, the mixture was further kept stirred for 3 hours at room temperature. It was then confirmed by thin-layer chromatography that an intermediate product was formed. The reaction mixture was filtrated to remove potassium carbonate, and then condensed under reduced pressure.

To the condensed reaction mixture, 50 mL of 1N aqueous solution of sodium hydroxide was added and stirred for 1 hour. Subsequently, after triphenylphosphine oxide formed as a bi-product was removed by filtration, concentrated hydrochloric acid was dropped to acidify the reaction mixture. The formed precipitates were collected by filtration, and then washed with a small amount of chloroform to obtain 1.2 g of 2-hydroxy-4-methoxycinnamic acid.

Successively, 1.2 g (6.2 mmol) of 2-hydroxy-4-methoxycinnamic acid was dissolved in 20 mL of dehydrated tetrahydrofuran in a 100 mL flask, and then 1.54 g (8 mmol) of 1-ethyl-3-(3-dimethylaminopropyl)carbodiimide hydrochloride was added therein. After the obtained mixture was stirred for 30 minutes, 922 mg (8 mmol) of 4-piperidinemethanol was further added therein.

The mixture was kept stirred to complete the reaction. The reaction mixture was condensed, and then dissolved in water. The resultant solution was subjected to extraction with chloroform, to obtain a crude product. The product was washed with 1N hydrochloric acid and saturated NaCl solution to obtain 121 mg of the aimed PBG-A1.

Synthesis Example 2 (Synthesis of Photo Base Generator PBG-A6)

The procedure of Synthesis example 1 was repeated except for using 841 mg (8 mmol) of diethanolamine in place of 922 mg (8 mmol) of 4-piperidinemethanol, to obtain 103 mg of PBG-A6.

Synthesis Example 3 (Synthesis of Photo Base Generator PBG-A7)

The procedure of Synthesis example 1 was repeated except for using 1.33 g (8 mmol) of 2-hydroxy-4-dimethylaminobenzaldehyde in place of 1.22 g (8 mmol) of 2-hydroxy-4-methoxybenzaldehyde, to obtain 108 mg of PBG-A7.

Synthesis Example 4 (Synthesis of Photo Base Generator PBG-A8 Hydrate)

The procedure of Synthesis example 1 was repeated except for using 1.33 g (8 mmol) of 2-hydroxy-4-dimethylaminobenzaldehyde and 841 mg (8 mmol) of diethanolamine in place of 1.22 g (8 mmol) of 2-hydroxy-4-methoxybenzaldehyde and 922 mg (8 mmol) of 4-piperidinemethanol, respectively, to obtain 90 mg of PBG-A8 anhydrate.

The PBG-A8 anhydrate obtained in Synthesis example 4 in an amount of 100 mg was dissolved in 50 mL of PGME, and 5 mL of pure water was added therein. The mixture was then heated and refluxed at 60° C. for 1 hour. After the mixture was cooled to room temperature, pure water was distilled off under reduced pressure to obtain a PGME solution of PBG-A8 hydrate.

Synthesis Example 6 (Synthesis of Polysiloxane (P1))

In a 2-L flask equipped with a stirrer, a thermometer and a cooling pipe, 24.5 g of a 25 mass % aqueous solution of tetramethylammonium hydroxide (TMAH), 300 ml of isopropyl alcohol (IPA) and 2.0 g of water were placed. Independently, 27.2 g (40 mol %) of methyltrimethoxysilane and 45.6 g (60 mol %) of tetramethoxysilane were mixed to prepare a mixed solution, which was then placed in a dropping funnel. The mixed solution was dropped into the flask at 60° C., and successively the obtained mixture was stirred at the same temperature for 3 hours. Subsequently, 10% HCl aqueous solution was added to neutralize the mixture, and then 200 ml of toluene and 300 ml of water were added into the neutralized mixture, so that the mixture was separated into two layers. The organic layer was condensed under reduced pressure to remove the solvent. To the obtained concentrate, PGMEA was added so that the solid content might be 40 mass %. The molecular weight (in terms of polystyrene reduced value) of the obtained polysiloxane (P1) was measured to find the mass average molecular weight (Mw)=8,800. The S2/S1 ratio, in which S1 and S2 are area intensities of absorption bands assigned to Si—O and SiOH, respectively, was measured to find S2/S1=0.15.

Examples 1 to 10 and Comparative Examples 1 to 4

Polysiloxane P1 and photo base generator PBG-A7 in amounts of 100 mass parts and 2.0 mass parts, respectively, were mixed and dissolved in 333 mass parts of PGME (solvent) to prepare a negative type photosensitive siloxane composition. The procedure was repeated except for changing various components as shown in Table 1, to prepare compositions of Examples 2 to 10 and Comparative examples 1 to 4.

With respect to each prepared composition, developability with an alkali developing solution, resolution, heat resistance and critical thickness for cracking were evaluated in the following manners. The results are shown in Table 1.

[Developability with an Alkali Developing Solution and Resolution]

Each prepared composition was dropped onto a silicon wafer, which was successively spin-coated at a rotation rate of 1,500 rpm and then pre-baked on a hot-plate at 100° C. for 90 seconds.

Thereafter, the coated wafer was subjected to exposure through a line-and-space pattern mask at 50 to 1,000 mJ/cm$^2$ by means of i-line exposure machine (NSR2205i11D, trade name, manufactured by Nikon Corporation). Successively, the wafer was subjected to post-exposure baking on a hot-plate at 120° C. for 60 seconds, then subjected to paddle development in which a 2.38% tetramethylammonium hydroxide (TMAH) aqueous solution was adopted as the developing solution, and finally rinsed with pure water to form a pattern. The obtained film was observed with an electron microscope (S-4700, trade name, manufactured by Hitachi High-Tech Fielding Corporation) to verify whether the pattern was formed or not. If the pattern was formed, the finest line-and-space in the resolved pattern was defined as the resolution of the composition.

[Heat Resistance]

Each prepared composition was dropped onto a silicon wafer, which was successively spin-coated at a rotation speed of 1,500 rpm and then pre-baked on a hot-plate at 100° C. for 90 seconds.

Thereafter, the coated wafer was subjected to entire surface exposure with 300 mJ/cm$^2$ (in terms of exposure amount at wavelength of 365 nm) using an ultraviolet visible light exposure machine such as an aligner. Successively, the wafer was subjected to post-exposure baking on a hot-plate at 120° C. for 60 seconds, to obtain a cured film. The cured film was then annealed for 30 minutes in a furnace under a nitrogen atmosphere. The annealing was performed on plural samples at different temperatures, which were selected in the range of 500 to 800° C. After cooled to room temperature, the annealed film was analyzed by FT-IR (FTIR-6100, trade name, manufactured by JASCO Corporation). IR absorption spectra of the samples annealed at different temperatures were evaluated to determine the temperature at which the peak attributed to $R^1$ in the formula (Ia) disappears and which was defined as the heat-resistance temperature

[Crack Threshold]

Each prepared composition was dropped onto a silicon wafer, which was successively spin-coated at a rotation speed of 1,500 rpm and then pre-baked on a hot-plate at 100° C. for 90 seconds.

Further, after the solid content of the composition was controlled, the composition was applied in the same manner to prepare plural samples different in thickness. Thereafter, the coated wafer was subjected to entire surface exposure with 300 mJ/cm$^2$ (in terms of exposure amount at wavelength of 365 nm) using an ultraviolet visible light exposure machine such as an aligner. Successively, the wafer was subjected to post-exposure baking on a hot-plate at 120° C. for 60 seconds, to obtain a cured film. The cured film was then annealed at 600° C. or 700° C. for 30 minutes in a furnace under a nitrogen atmosphere. After cooled to room temperature, the annealed film was observed with an optical microscope to check whether cracks were formed or not. On the basis of the observation, the thickness of the thickest sample in which no cracks were formed was defined as the critical thickness for cracking.

TABLE 1

| | polysiloxane | | | | | | | | | | |
| | | mixing ratio of monomers (mol %) | | | mass average molecular | | photo base | | alkali | resolution | heat resistance | critical thickness for cracking |
| | compound | i-1 | i-2 | i-3 | weight | S2/S1 | generator | additives | developability | (μm) | (° C.) | (μm) |
|---|---|---|---|---|---|---|---|---|---|---|---|---|
| Ex. 1 | P1 | 40 | — | 60 | 8800 | 0.15 | PBG-A7 | — | possible | 3.0 | 750 | 1.2 |
| Ex. 2 | P2 | 70 | — | 30 | 4500 | 0.13 | PBG-A2 | — | possible | 3.0 | 750 | 2.8 |
| Ex. 3 | P3 | 50 | — | 50 | 6500 | 0.12 | PBG-A3 | — | possible | 3.0 | 750 | 1.4 |
| Ex. 4 | P2 | 70 | — | 30 | 4300 | 0.10 | PBG-A1 | — | possible | 2.0 | 750 | 2.8 |
| Ex. 5 | P3 | 50 | — | 50 | 6300 | 0.10 | PBG-A4 | — | possible | 1.8 | 750 | 1.4 |
| Ex, 6 | P2 | 70 | — | 30 | 4200 | 0.08 | PBG-B1 | diethylthio-xanthone | possible | 1.2 | 750 | 2.8 |
| Ex. 7 | P2 | 70 | — | 30 | 4200 | 0.07 | PBG-A5 | — | possible | 1.0 | 750 | 2.8 |
| Ex. 8 | P2 | 70 | — | 30 | 4000 | 0.06 | PBG-B2 | diethylthio-xanthone | possible | 0.5 | 750 | 2.8 |
| Ex. 9 | P4 | 80 | — | 20 | 1800 | 0.06 | PBG-A8 hydrate | — | possible | 1.0 | 750 | 3.0 |
| Ex. 10 | P5 | 60 | 10 | 30 | 2400 | 0.05 | PBG-A6 | — | possible | 0.5 | 650 | 1.2 |
| Com. 1 | P2 | 70 | — | 30 | 3200 | 0.04 | PBG-A1 | — | impossible (not dissolved) | — | — | — |
| Com. 2 | P2 | 70 | — | 30 | 4800 | 0.16 | PBG-A1 | — | impossible (entirely dissolved) | — | — | — |
| Com. 3 | P2 | 70 | — | 30 | 4300 | 0.10 | DECAM | — | impossible (entirely dissolved) | — | — | — |
| Com. 4 | P2 | 70 | — | 30 | 4300 | 0.10 | — | — | impossible (entirely dissolved) | — | — | — |

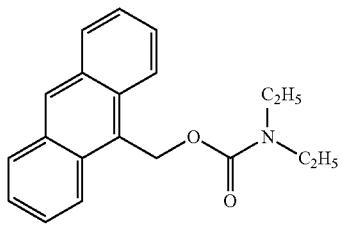 [SMILES: CCN(CC)C(=O)OCc1c2ccccc2cc2ccccc12]

DECAM: 9-anthrylmethyl N,N-diethylcarbamate

From the above results, the composition of the present invention was confirmed to make it possible to form a thick and highly heat resistant cured film.

The invention claimed is:

1. A negative type photosensitive siloxane composition, comprising:
   (I) a polysiloxane
   which contains a repeating unit represented by the following formula (Ia):

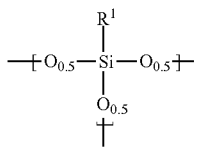

wherein
   $R^1$ is hydrogen, a monovalent to trivalent, linear, branched or cyclic, saturated or unsaturated $C_{1-30}$ aliphatic hydrocarbon group, or a monovalent to trivalent $C_{6-30}$ aromatic hydrocarbon group,
   in said aliphatic hydrocarbon group and said aromatic hydrocarbon group, one or more methylene are unsubstituted or substituted with oxy, imide or carbonyl, one or more hydrogens are unsubstituted or substituted with fluorine, hydroxy or alkoxy, or one or more carbons are unsubstituted or substituted with silicon, when $R^1$ is divalent or trivalent, $R^1$ connects Si atoms contained in a plurality of repeating units; and
   a repeating unit represented by the following formula (Ib):

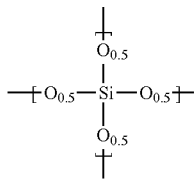

and further
   which shows a spectrum in which the area intensities S1 and S2 of the peaks in the ranges of $1100\pm100$ cm$^{-1}$ and $900\pm100$ cm$^{-1}$ assigned to Si—O and SiOH, respectively, are in a S2/S1 ratio of 0.05 to 0.15 when measured and analyzed by FT-IR, (II) a photo base generator
   represented by the following formula (PBG-A) or (PBG-B):

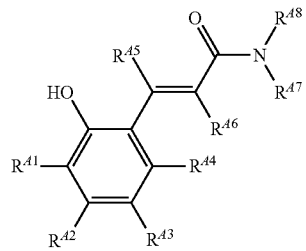

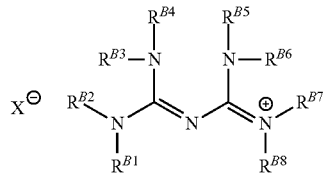

wherein
   each of $R^{A1}$ to $R^{A6}$ is independently hydrogen, halogen, hydroxy, mercapto, sulfide, silyl, silanol, nitro, nitroso, sulfino, sulfo, sulfonate, phosphino, phosphinyl, phosphono, phosphonato, amino, ammonium, an unsubstituted or substituted $C_{1-20}$ aliphatic hydrocarbon group, an unsubstituted or substituted $C_{6-22}$ aromatic hydrocarbon group, unsubstituted or substituted $C_{1-20}$ alkoxy, or unsubstituted or substituted $C_{6-20}$ aryloxy;
   each of $R^{A7}$ and $R^{A8}$ is independently $C_{1-6}$ hydroxyalkyl;
   each of $R^{B1}$ to $R^{B8}$ is independently hydrogen, an unsubstituted or substituted $C_{1-20}$ aliphatic hydrocarbon group, an unsubstituted or substituted $C_{6-22}$ aromatic hydrocarbon group, unsubstituted or substituted $C_{1-20}$ alkoxy, or unsubstituted or substituted $C_{6-20}$ aryloxy; and
   X$^-$ is a borate or carboxylate ion having an unsubstituted or substituted $C_{1-20}$ aliphatic hydrocarbon group or an unsubstituted or substituted $C_{6-22}$ aromatic hydrocarbon group; and
   (III) a solvent.

2. The composition according to claim 1, wherein said polysiloxane has silanol at the terminal or in the side chain.

3. The composition according to claim 1, wherein said $R^1$ is hydrogen, a linear, branched or cyclic $C_{1-6}$ alkyl or a $C_{6-10}$ aryl.

4. The composition according to claim 1, wherein said polysiloxane comprises repeating units (i-1) and (i-3) and optionally (i-2):

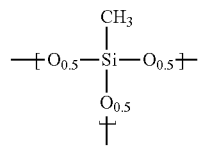

-continued (i-2)

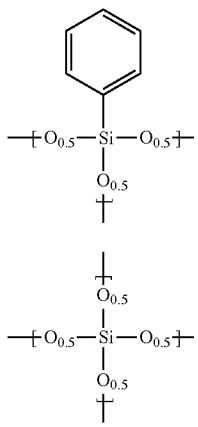

(i-3)

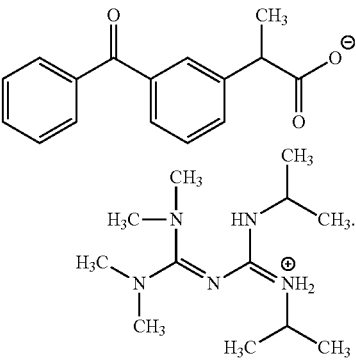
(PBG-B2)

provided that the mixing molar ratios p1, p2 and p3 of (i-1), (i-2) and (i-3), respectively, satisfy the conditions of:

$0.04 \leq p1 \leq 0.8$, $0 \leq p2 \leq 0.4$, and $0.2 \leq p3 \leq 0.6$.

5. The composition according to claim 1, wherein said polysiloxane has a mass average molecular weight of 1,000 to 10,000.

6. The composition according to claim 1, wherein said polysiloxane contains the repeating unit (Ib) in a mixing ratio of 20 mol % or more based on the total amount of the repeating units.

7. The composition according to claim 1, wherein said photo base generator is selected from the group consisting of the following (PBG-A6), (PBG-A7), (PBG-B1) and (PBG-B2):

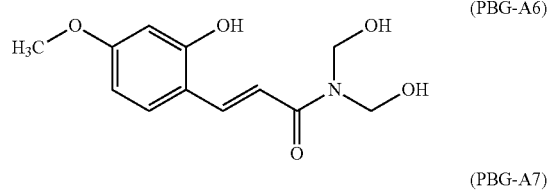
(PBG-A6)

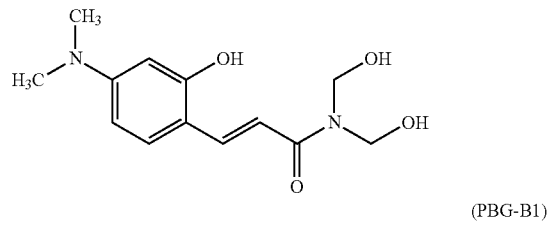
(PBG-A7)

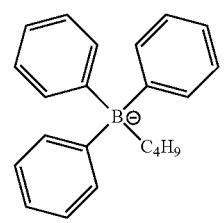
(PBG-B1)

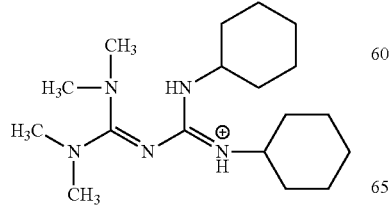

8. The composition according to claim 1, wherein the amount of said photo base generator is 0.1 to 5.0 mass % based on the mass of the polysiloxane contained in the composition.

9. The composition according to claim 1, wherein the solid content is 2.0 to 50 mass % based on the total mass of the composition.

10. A method for producing a cured film, comprising: coating a substrate with the composition according to claim 1, exposing the substrate to light, then developing and heating the substrate.

11. The method for producing a cured film according to claim 10, wherein the heating step is carried out at a temperature of 500° C. or above.

12. The method for producing a cured film according to claim 10, wherein said cured film has a thickness of 1.0 μm or more.

13. A method for producing an electronic device, including the method for producing a cured film according to claim 1.

14. The composition according to claim 1, wherein the ratio of the S2/S1 ratio is 0.06 to 0.13.

15. The composition according to claim 7, wherein the ratio of the S2/S1 ratio is 0.06 to 0.13.

16. A negative type photosensitive siloxane composition, consisting essentially of:
(I) a polysiloxane
which contains a repeating unit represented by the following formula (Ia):

(Ia)

wherein
R¹ is hydrogen, a monovalent to trivalent, linear, branched or cyclic, saturated or unsaturated $C_{1-30}$ aliphatic hydrocarbon group, or a monovalent to trivalent $C_{6-30}$ aromatic hydrocarbon group,
in said aliphatic hydrocarbon group and said aromatic hydrocarbon group, one or more methylene are unsubstituted or substituted with oxy, imide or carbonyl, one or more hydrogens are unsubstituted or substituted with fluorine, hydroxy or alkoxy, or one or more carbons are unsubstituted or substituted with silicon, when $R^1$ is divalent or trivalent, le connects Si atoms contained in a plurality of repeating units; and a repeating unit represented by the following formula (Ib):

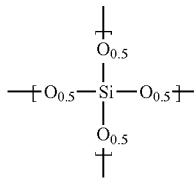

(Ib)

and further which shows a spectrum in which the area intensities S1 and S2 of the peaks in the ranges of 1100±100 cm$^{-1}$ and 900±100 cm$^{-1}$ assigned to Si—O and SiOH, respectively, are in a S2/S1 ratio of 0.05 to 0.15 when measured and analyzed by FT-IR, (II) a photo base generator represented by the following formula (PBG-A) or (PBG-B):

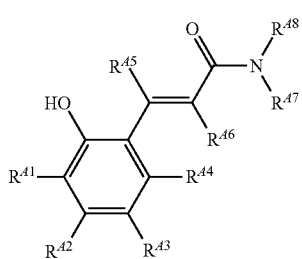

(PBG-A)

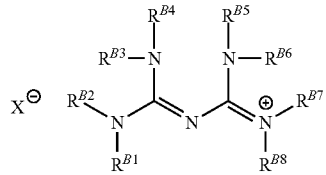

(PBG-B)

wherein each of $R^{A1}$ to $R^{A6}$ is independently hydrogen, halogen, hydroxy, mercapto, sulfide, silyl, silanol, nitro, nitroso, sulfino, sulfo, sulfonate, phosphino, phosphinyl, phosphono, phosphonato, amino, ammonium, an unsubstituted or substituted $C_{1-20}$ aliphatic hydrocarbon group, an unsubstituted or substituted $C_{6-22}$ aromatic hydrocarbon group, unsubstituted or substituted $C_{1-20}$ alkoxy, or unsubstituted or substituted $C_{6-20}$ aryloxy;

each of $R^{A7}$ and $R^{A8}$ is independently $C_{1-6}$ hydroxyalkyl;

each of $R^{B1}$ to $R^{B8}$ is independently hydrogen, an unsubstituted or substituted $C_{1-20}$ aliphatic hydrocarbon group, an unsubstituted or substituted $C_{6-22}$ aromatic hydrocarbon group, unsubstituted or substituted $C_{1-20}$ alkoxy, or unsubstituted or substituted $C_{6-20}$ aryloxy; and $X^-$ is a borate or carboxylate ion having an unsubstituted or substituted $C_{1-20}$ aliphatic hydrocarbon group or an unsubstituted or substituted $C_{6-22}$ aromatic hydrocarbon group; and (III) a solvent.

17. The composition according to claim 16, wherein the ratio of the S2/S1 ratio is 0.06 to 0.13.

* * * * *